(12) United States Patent
Gipp et al.

(10) Patent No.: US 7,170,973 B2
(45) Date of Patent: Jan. 30, 2007

(54) APPARATUS AND METHOD FOR REDUCING IMAGE ARTIFACTS

(75) Inventors: Thomas Gipp, Hürth (DE); Hans-Aloys Wischmann, Henstedt-Ulzburg (DE); Falko Busse, Aachen (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 128 days.

(21) Appl. No.: 10/513,276

(22) PCT Filed: Apr. 29, 2003

(86) PCT No.: PCT/IB03/01638

§ 371 (c)(1), (2), (4) Date: May 25, 2005

(87) PCT Pub. No.: WO03/094733

PCT Pub. Date: Nov. 20, 2003

(65) Prior Publication Data

US 2005/0238139 A1  Oct. 27, 2005

(30) Foreign Application Priority Data

May 7, 2002 (DE) .............................. 102 20 293

(51) Int. Cl.
*H05G 1/64* (2006.01)

(52) U.S. Cl. ..................................... 378/98.8; 378/98.3
(58) Field of Classification Search ......... 378/97–98.8; 250/580, 591
See application file for complete search history.

(56) References Cited

U.S. PATENT DOCUMENTS

| 5,905,772 A * | 5/1999 | Rutten et al. ............... 378/98.8 |
| 6,600,159 B2 * | 7/2003 | Overdick et al. ...... 250/370.11 |
| 6,885,725 B2 * | 4/2005 | Suzuki ......................... 378/19 |
| 6,965,111 B2 * | 11/2005 | Endo ..................... 250/370.11 |

FOREIGN PATENT DOCUMENTS

WO    WO 98 01992    1/1998

* cited by examiner

*Primary Examiner*—Edward J. Glick
*Assistant Examiner*—Jurie Yun

(57) ABSTRACT

The invention relates to an X-ray apparatus for forming X-ray images, which apparatus includes an X-ray detector (4) for the conversion of X-rays into electrical signals, a detector exposure unit (5) for the emission of electromagnetic radiation in dependence on how first and second exposure parameters, the value of the first exposure parameters being defined by the acquisition mode whereas the second exposure parameters are not defined by the acquisition mode, and also a control unit (13) for changing and controlling at least one second exposure parameter of the detector exposure unit upon a change of the acquisition mode.

10 Claims, 4 Drawing Sheets

APPARATUS AND METHOD FOR REDUCING IMAGE ARTIFACTS

Figure 1:
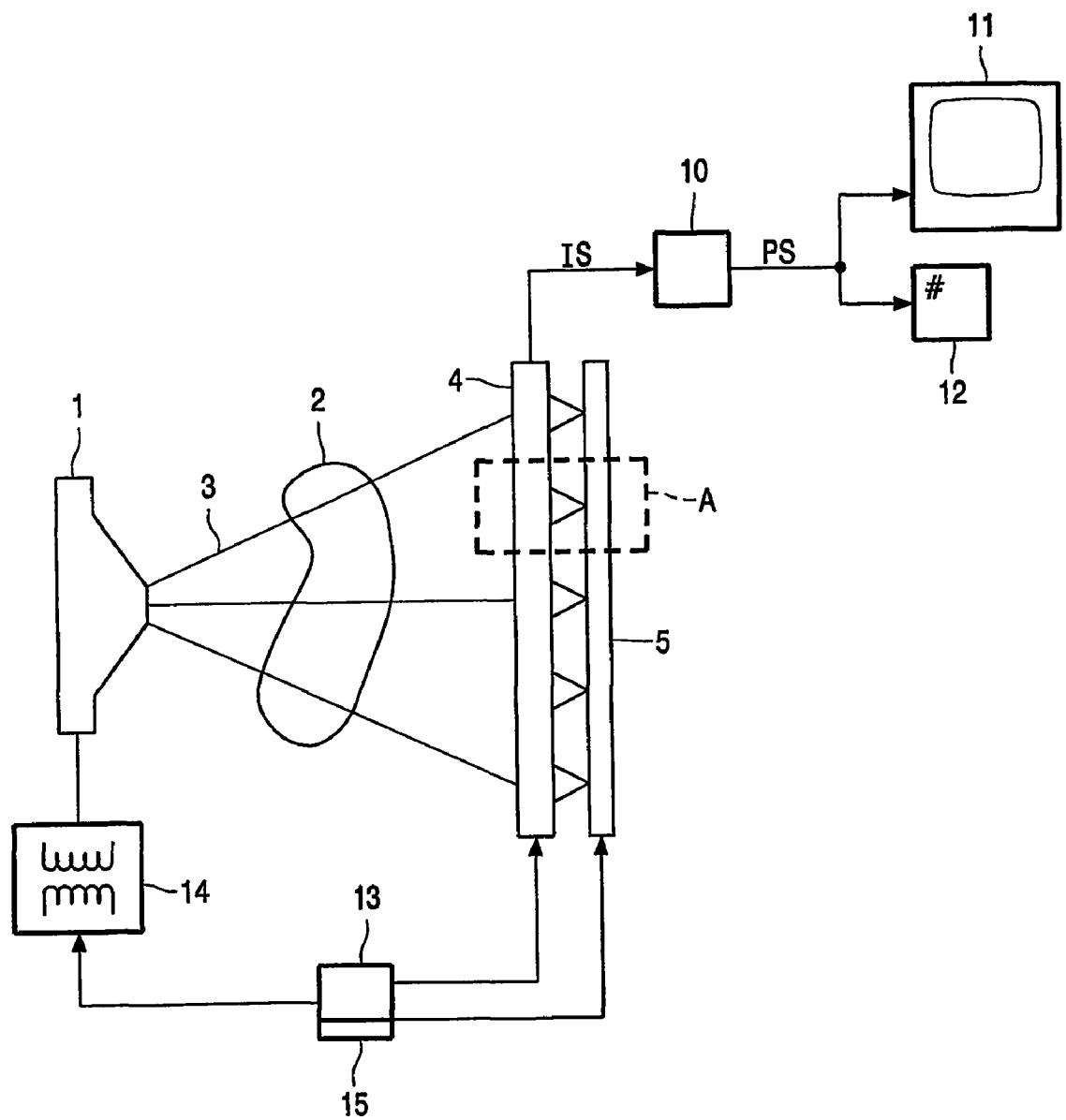

The invention relates to an apparatus and a method for reducing image artifacts for X-ray detectors.

X-ray detectors are devices, which convert X-rays into a typically electronic signal, which can be evaluated. An X-ray signal acquired at an instant is referred to as an X-ray image. An X-ray image consists of at least one X-ray signal value. A temporal succession of X-ray images is referred to as an X-ray image sequence.

X-ray detectors are used inter alia in imaging X-ray apparatus in the medical field. Contemporary detectors utilize, for example, a conversion layer which consists mainly of a scintillation material which absorbs the X-rays and emits optical light quanta essentially in proportion to the incident overall energy of the X-rays. The scintillation material is typically attached, by way of an optically transparent adhesive, to a photodiode, which is based on a semiconductor material such as silicon, or to a one-dimensionally or two-dimensionally structured photodiode arrangement, or is vapor-deposited thereon. The photodiode arrangement may additionally include electronic devices for the reading out, amplification and digitization of the photodiode signals. The photodiodes absorb optical quanta and convert such quanta into charge carriers. The charge carriers are read out and can be converted into a voltage. An X-ray signal value is also referred to as a pixel value. A pixel typically represents an image point.

Other X-ray detectors may be made, for example, of directly-converting materials. An X-ray detector may be capable of counting individual X-ray quanta or of integrating the incident X-ray energy.

The photodiode or the photodiode arrangement of the X-ray detector may be made of silicon, in which case crystalline, polycrystalline or amorphous silicon may be used. X-ray detectors having a particularly large surface area, for example, as used in contemporary radiography, can be manufactured when use is made of amorphous silicon (a-Si:H). When the light quanta emitted, for example, by the scintillation material are converted, charge carriers are raised from the valence band of the a-Si:H to the conduction band. The free charge carriers can be read out. The a-Si:H, however, has a large number of local capture states between the bands, in which capture states charge carriers are retained for some time before they are emitted again, for example, due to thermal excitation. In the case of X-ray image sequences the foregoing causes the X-ray detector to exhibit so-called afterglow, which is dependent on the local radiation history. As a result, each pixel contains signal components, which do not belong to the charge carriers directly generated in the instantaneous irradiation period. If a part of the detector was strongly irradiated in a preceding image and is exposed to a small number only of X-ray quanta in the instantaneous irradiation period, the afterglow signal may have a decisive effect on the overall signal. This gives rise to partly unusable images. Such signal components of the X-ray image are also referred to as image artifacts. Such incorrect images cannot be tolerated, that is, notably in the case of irradiation of human patients, because the applied X-ray dose should be converted as well as possible into usable medical data and may not be applied unnecessarily.

An X-ray detector is often used to acquire temporal sequences of X-ray images. The values of the acquisition parameters, such as image acquisition time, detector resolution and X-ray exposure time, govern the acquisition mode in which the sequence is acquired. It is often desirable to change at least one acquisition parameter in the course of an X-ray image sequence so as to achieve adaptation to the changing requirements, for example, during an interventional examination, that is, for example, in the case of the X-ray images acquired during a surgical intervention in a patient. The changing of one acquisition parameter leads to another detection mode.

WO 98/01992 discloses an X-ray apparatus, which includes not only the X-ray detector and an X-ray source, but also an additional source of radiation, which emits electromagnetic radiation. Such an additional radiation source (also referred to as a bias light source) can be used to fill, prior to and/or during the X-ray exposure, the capture states in the a-Si:H by additional application of a homogeneous light signal, so that the signal generated by the X-ray exposure ultimately cannot lose charge carriers to the already filled capture states, meaning that the X-rays are also directly converted into readable charge carriers. The additional signal emitted by the filled capture states is homogeneous to a high degree and does not give rise to a noticeable degradation of the image. WO 98/01992 explains that a change of the acquisition parameters (for example, image acquisition time, detector resolution etc.), that is, a change of the acquisition mode, may lead to a change of the dynamic equilibrium of the charge carriers moved to the capture states by the additional light and the charge carriers emitted thereby. This necessarily leads to image artifacts, because the background signal from the capture states forms part of the offset signal to be subtracted. The absolute value of the offset signal, however, is determined in the state of the equilibrium. In order to avoid image artifacts, WO 98/01992 proposes to abstain from changing the acquisition parameters; this means a distinct limitation of the usability and flexibility of the apparatus.

In given circumstances, for example, in the case of an intervention, it may be necessary to change from one acquisition mode to another. This leads to an imbalance of the ratio of the captured and the emitted charge carriers and hence to image artifacts after such a change.

Therefore, it is an object of the present invention to provide an apparatus and a method whereby undesirable image artifacts can be reduced for an X-ray detector.

The object is achieved by means of an X-ray apparatus for the acquisition of X-ray images, which apparatus includes an X-ray detector for the conversion of X-rays into electrical signals, a detector exposure unit for the emission of electromagnetic radiation in dependence on first and second exposure parameters, the value of the first exposure parameters being defined by the acquisition mode whereas the second exposure parameters are not defined by the acquisition mode, and also a control unit for changing and controlling at least one second exposure parameter of the detector exposure unit upon a change of the acquisition mode.

In order to obtain an as good as possible image, in the case of digital X-ray detectors two essential corrections are performed after the acquisition: first an offset signal is subtracted and subsequently gain standardization is performed. The offset signal is composed of inter alia leakage currents and charge carriers emitted from the capture states. Furthermore, there are also afterglow effects in the scintillation material. The offset image, that is, the offset signals for each pixel in the relevant acquisition mode, are measured in the steady state and stored so that during the acquisition sequence it can be used to subtract the offset signal from the image signal. The acquisition mode is determined by the acquisition parameters. Acquisition parameters are, for example, the image acquisition time, the detector resolution and the X-ray exposure time. The X-rays are applied to the X-ray detector typically in a pulsed fashion. In that case there is time between the pulses to read out the pixel signals and also for a subsequent electronic reset during which the residual charge is drained from the photodiode. During the reset operation preferably the additional detector exposure unit which emits bias light is activated, so that the charge carriers produced by the detector exposure, not being excited in a capture state, are also drained. It is possible to utilize bias light of a wavelength such that the charge carriers cannot be raised to the conduction band. Such a bias light can be applied continuously.

When the state density function of the capture states is in a non-steady state, the offset signal measured in the steady state does not represent the instantaneous offset value. When the new steady state is reached, after the offset subtraction there will be a signal background which leads to additional noise and a reduction of the dynamic range. In many cases the image will no longer be suitable for medical evaluation.

The gain normalization ensures that a uniformly irradiated X-ray detector produces a uniform output signal, irrespective of the properties of the detector pixels. The quality of the gain normalization may also be adversely affected by a non-steady state of the capture states.

A change of an acquisition parameter typically gives rise to a non-steady state in the ratio of the charge carriers excited by the additional illumination from the valence band in a capture state to the charge carriers emitted again from the capture states. When the acquisition sequence with the new acquisition parameters lasts long enough, a new steady state will be asymptotically reached.

The value of first exposure parameters of the detector exposure unit is defined by the acquisition mode. For example, the bias light pulse spacing must be changed in conformity with the image acquisition time when the bias light pulse is to occur in the reset phase. The values of second exposure parameters, such as the exposure intensity or the exposure time, are not defined by the change of the acquisition mode. A further second exposure parameter is the exposure wavelength composition. The wavelength composition of the bias light can be controlled when at least two bias light sources of different wavelength or a means for changing the wavelength of a light source are available.

The problem posed by the occurrence of image artifacts after a change of the acquisition mode is dealt with in accordance with the invention in that at least one second exposure parameter of the detector exposure unit is changed and controlled upon a change of the acquisition mode which is determined by exposure parameters, that is, in such a manner that the new steady state to be reached deviates as little as possible from the previous steady state, thus producing a small artifact signal only.

In order to carry out the changing and the control of the exposure parameters, use is made of a control unit which has knowledge of the exposure parameters before and after the change of mode, so that it can perform the appropriate control in respect of the changing and controlling of the exposure parameters of the exposure unit.

In the case of nuclear medical examinations, a radioactive marking material is injected into the patient so that the patient himself becomes an X-ray source. Radiographic X-ray apparatus, however, have an X-ray source for X-ray exposure of the patient. This is described in claim 2.

The control unit is preferably also suitable to control the X-ray detector and an X-ray source which possibly forms part of the X-ray apparatus. This offers the advantage that the control of all system components is incorporated in one component and that corresponding parameters are available for all control and regulating operations. The additional control of components of the X-ray apparatus is disclosed in claim 3.

The acquisition parameters governing an acquisition mode include the image acquisition time, the X-ray exposure time and the detector resolution. This is dealt with in claim 4.

The exposure intensity, the exposure time and the exposure wavelength composition are particularly expressive exposure parameters. This is disclosed in claim 5.

In accordance with the invention it is advantageous when the changing and control of a second exposure parameter, for example, the exposure time, take place in proportion to the changing of an acquisition parameter, for example, the image acquisition time. This is because when, for example, the image acquisition time is prolonged, the integral bias light intensity is reduced in proportion to the prolongation. A corresponding proportional prolongation of the exposure time results in the same integral bias light intensity as before the changing of the acquisition parameter and hence in a substantially the same steady state of the capture state density function in the new exposure mode. This proportional change is dealt with by claim 6.

Furthermore, in accordance with the invention it is advantageous when the changing and control of the exposure parameters after a change of the acquisition mode take place as a function of time. As has already been described, there are additional effects due to the scintillation material or other detector elements. In order to counteract such effects or to achieve a particularly advantageous approach for reaching a steady state, the exposure parameters are controlled as a function of time, that is, from one image to the next the second exposure parameters are adjusted differently after the changing of at least one acquisition parameter. The corresponding variations in time of the exposure can be determined experimentally, for example, by means of defined calibration images formed on the detector. The control should converge towards a constant final value. This is disclosed in claim 7.

It is particularly advantageous when the changing and control values of the exposure parameters which have been determined in advance are stored in a table which can be read by the control unit, so that the changing and control for a given change of the acquisition mode take place by means of the values from this table. This is described in claim 8.

As has already been stated, an X-ray detector typically operates in a pulsed mode and the detector exposure unit is active only in the reset phases, thus ensuring the draining of the charge carriers produced. This advantageous embodiment is disclosed in claim 9.

Claim 10 discloses a method in accordance with the invention for enhancing the image quality. The X-ray detector is irradiated by means of X-rays in a pulsed or continuous manner. Additionally, the X-ray detector is exposed to bias light from the detector exposure unit. This exposure can take place during the continuous irradiation by means of X-rays within the phases in which the X-ray detector is not exposed to X-rays, that is, preferably in the reset phase. In the case of a change of the acquisition mode, a control unit changes and controls at least one second exposure parameter in such a manner that the steady state of the capture states can be adjusted with as little change as possible. The charge carriers generated in the detector pixels are read out and converted, for example, into a current signal or a voltage signal. The signals thus acquired can also be digitized.

Figure 2:
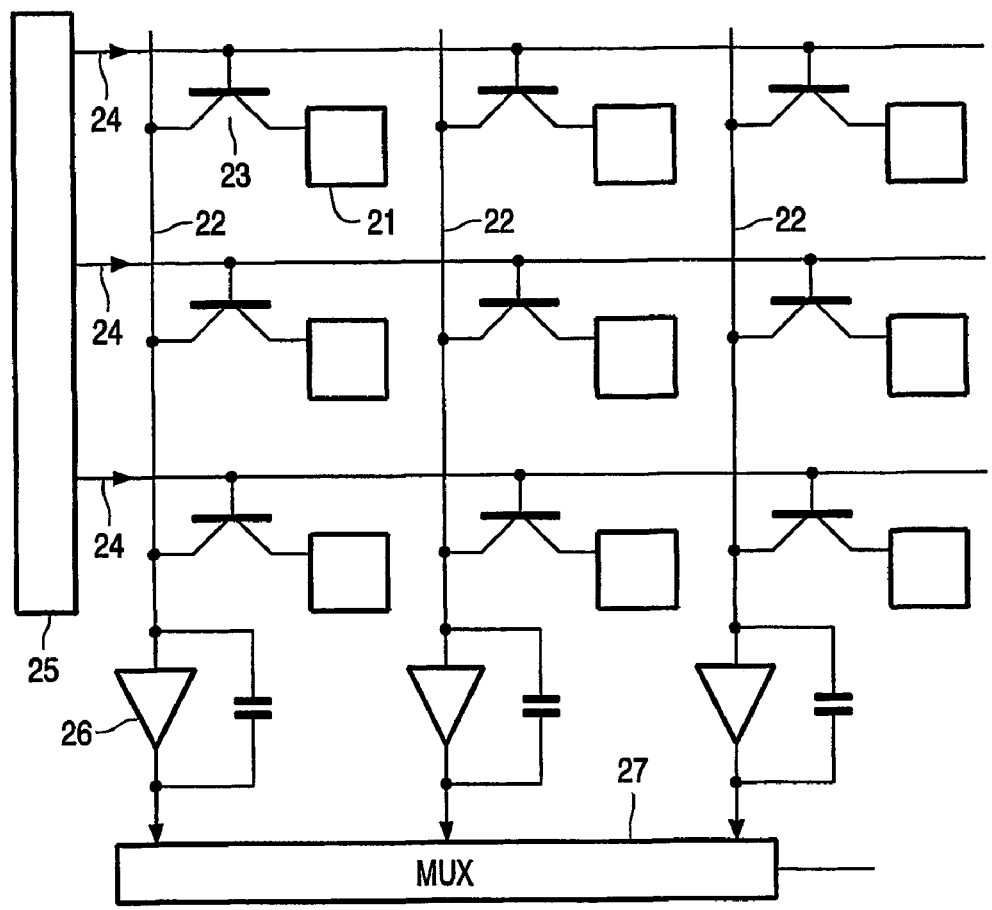
Figure 3:
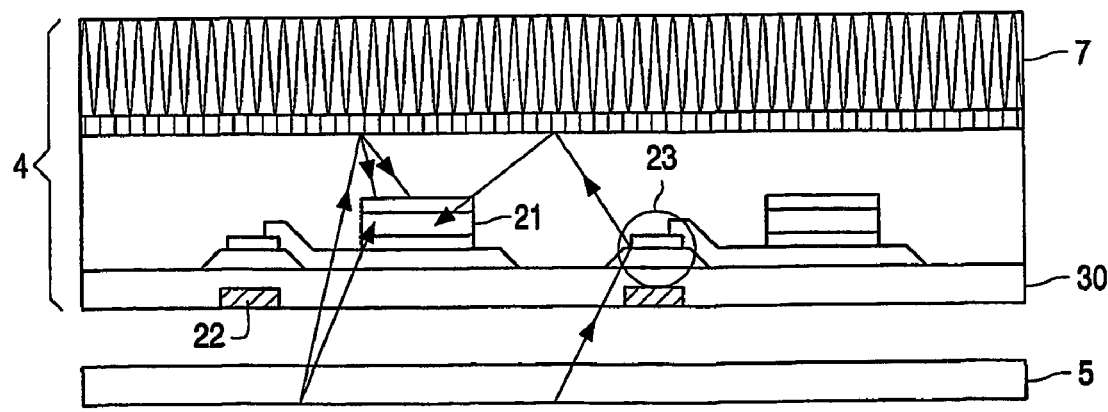
Figure 4:
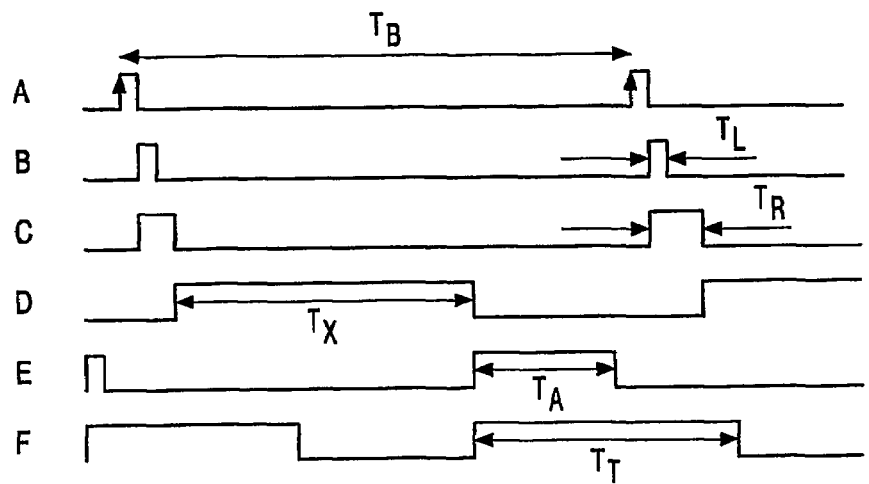
Figure 5:
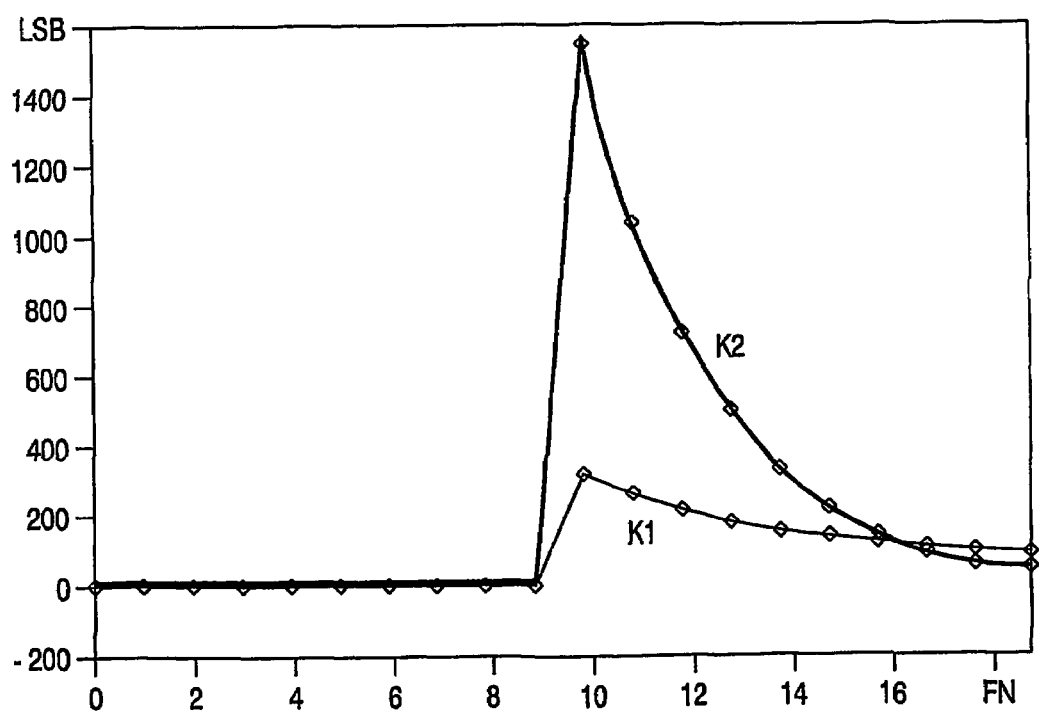
Figure 6:
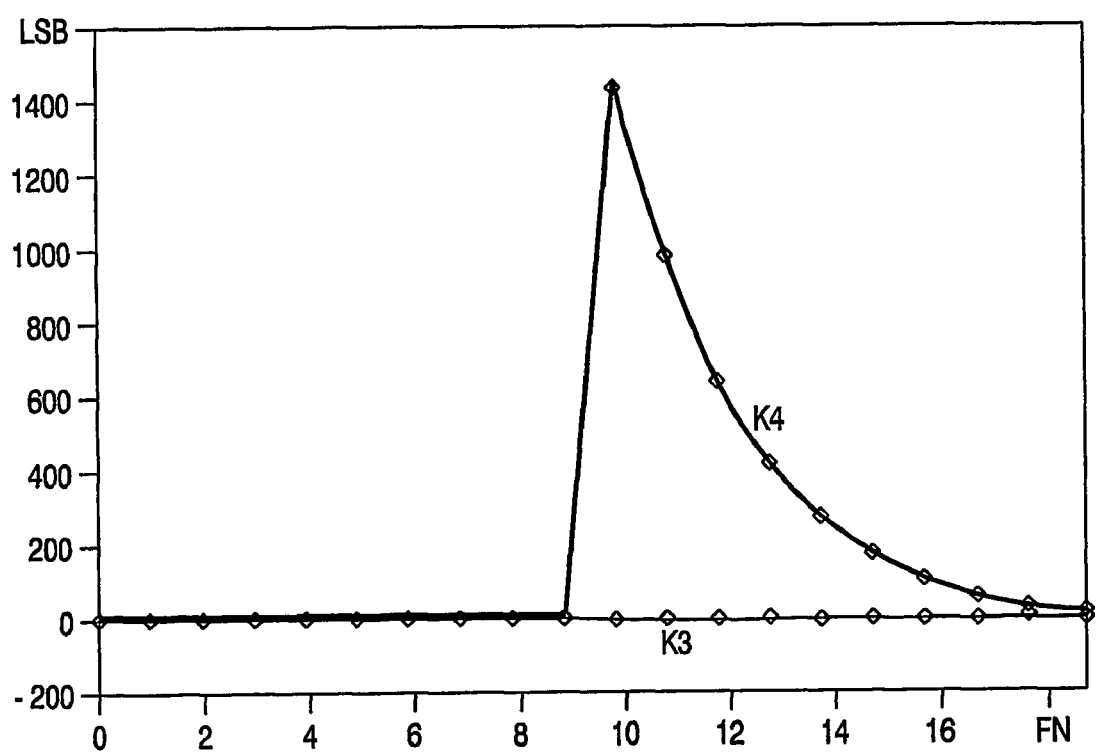

An embodiment of the invention will be described in detail hereinafter with reference to some Figures. Therein:

FIG. 1 is a diagrammatic representation of an X-ray apparatus in accordance with the invention, FIG. 2 is a diagrammatic representation of a part of a two-dimensional photodiode arrangement, FIG. 3 is a diagrammatic cross-sectional view of a detector of the X-ray apparatus in accordance with the invention, which detector is provided with a bias light source, FIG. 4 shows a part of a time diagram for controlling the X-ray apparatus in accordance with the invention, FIG. 5 shows a variation of the mean value, corrected by means of an offset signal, of a dark image before and after the changing of an acquisition parameter, and FIG. 6 shows the variation of the mean value of FIG. 5 after the changing and control of the exposure parameter in accordance with the invention.

FIG. 1 shows an X-ray apparatus, which includes an X-ray source 1, which irradiates an object 2, notably a patient to be radiologically examined, by means of an X-ray beam 3. X-rays which are not absorbed are converted into an electronic image signal IS by an X-ray detector 4. The image signal is applied to an image processing unit 10, which outputs an image signal current PS which corresponds to a processed X-ray image. The processed X-ray image can be stored in a storage medium 12 and/or be displayed on a display screen 11. A bias light source 5 is arranged behind the detector 4 and exposes the detector to bias light in conformity with the exposure parameters imposed by the control unit 13. The control unit 13 in this embodiment controls not only the bias light source 5 but also the X-ray detector 4 and the X-ray source 1, that is, the latter via the high-voltage generator 14. The control unit 13 also includes a memory 15 which is used to store data and tables for the changing and control of parameters of the X-ray apparatus (for example, X-ray apparatus acquisition parameters and exposure parameters) and to read out such data and tables at a later stage again.

The bias light source 5 may be formed in known manner, for example, as a matrix of LEDs. An additional diffuser (not shown) ensures that the exposure is very homogeneous. A further embodiment consists of a matrix, which comprises two types of LEDs which are arranged, for example, in a checkerboard fashion and which emit light of a different respective wavelength. This enables particularly flexible variations of the detector exposure and hence constitutes an advantageous possibility for counteracting image artifacts.

FIG. 2 is a diagrammatic representation of a part of a two-dimensional detector arrangement. The Figure shows 3×3 photodiodes 21. X-ray detectors may have a matrix size of 100×200, 1024×1024, 2000×2000 photodiodes or another size. The photodiodes 21 absorb incident optical light quanta and convert these quanta into charge carriers. The row driver circuit 25 controls the switching elements 23 (in this case formed by switching transistors) via address leads 24 and the collected charge carriers of the photodiodes of one row are applied, when the switching elements 23 are switched on, to integrating amplifier elements 26 via respective read-out leads 22; finally, a multiplexer circuit 27 successively switches through the individually present voltages. Possibly after further steps, for example, digitization, the image signal current IS is obtained. The row driver circuit is coupled to the control unit 13, thus enabling control of the row sequencing.

FIG. 3 is a detailed cross-sectional view of the part A (denoted by dashed lines in FIG. 1) of the X-ray detector 4 and the bias light source 5 arranged behind the detector. The scintillator 7 absorbs incident X-rays and emits light quanta. The Figure show light quanta emitted by the bias light source 5 can be incident, directly or indirectly, on the photodiode structure 21 via a preferably transparent substrate 30, for example, a substrate made of glass.

FIG. 4 shows a part of a time diagram of an X-ray apparatus. The line A of the diagram shows the image triggering; the ascending arrow indicates that in this case ascending edge triggering is concerned. The image acquisition time, that is, the period of time elapsing between two image trigger pulses, is denoted by the reference $T_B$. The line B of the diagram shows the duration of the exposure by the detector exposure unit, which duration is denoted by the value $T_L$. The line C of the diagram indicates the duration of the electronic reset (denoted by the reference $T_R$) during which all charge carriers are drained from the photodiodes. The line D of the diagram shows the X-ray exposure time (referred to as $T_X$); the line E of the diagram shows the image signal read-out phase during which the X-ray image signals are read out during the read-out period $T_A$, and the line F of the diagram shows the image transmission time during which the image signals are applied to the image processing unit (transmission time $T_T$). Granted, the distance in time between the bias light pulses is also an exposure parameter. However, because the bias light pulse in the preferred embodiment can occur only during the electronic reset phase, the distance in time of the bias light pulses is an exposure parameter whose value is determined by the acquisition mode. When the image acquisition time $T_B$ changes, the value of the distance in time between the bias light pulses must also change in order to ensure that the bias light pulses still occur within the reset phase. In the present example the bias light pulse spacing is defined as the image acquisition time $T_B$. Such exposure parameters, imposed by the acquisition mode, form part of the group of first parameters which are not available for the control and regulating by the control unit.

TABLE 1

Various acquisition modes of a digital X-ray detector used for cardiac examinations.

| No. | Mode | Detector resolution | Effective image size [mm²] | Max. image rate [images/s] | Max. Tx [ms] |
|---|---|---|---|---|---|
| 1 | Full image, pulsed | 1 × 1 | 176 × 176 | 30 | 19.5 |
| 2 | Full image, combined, pulsed | 2 × 2 | 176 × 176 | 60 | 8.0 |
| 3 | Full image, continuous | 1 × 1 | 176 × 176 | 30 | continuous |
| 4 | Zoom, | 1 × 1 | 110 × 110 | 60 | 6.5 |

Table 1 shows various acquisition modes for a digital X-ray detector, which has been configured especially for cardiac examinations. This detector has an active surface area of 176×176 mm². Column 1 contains the number of the acquisition mode of the present selection. Column 2 provides a brief description of the acquisition mode. In the case of "full image", all pixels contribute to the image; in the case of "zoom", only a limited part of the photodiode arrangement contributes to the image. "Pulsed" means that the X-rays are emitted in a pulsed fashion by the X-ray source 1 whereas "continuous" means that X-rays are emitted continuously. "Combined" describes an acquisition mode in which a plurality of pixels are combined so as to form one image point; in this case 2×2 pixels are combined so as to form one image point. In the combined mode reading out can be faster and the image points have a better signal-to-noise ratio. Column 3 indicates the detector resolution, that is, it specifies how combination takes place. Column 4 shows the effective image size in mm². Column 5 states the maximum image rate, that is, the maximum number of X-ray images that can be read out per second in the case of a sequence acquisition. The last column indicates the maximum X-ray exposure time $T_X$ in ms at the maximum image rate.

Different acquisition parameters are adjusted in the various modes. For example, it is possible to combine photodiodes so as to provide an effectively larger image point at the photodiode level. This offers special advantages for applications involving a smaller applied X-ray rate per image; the larger image point then means a less favorable resolution, but also a better signal-to-noise ratio. In the mode 2 with combined pixels a higher maximum image rate per second is obtained because of the smaller number of image signal values to be read out. On the basis of the read-out time $T_A$ and the reset time $T_R$ a maximum X-ray exposure time $T_X$ per image is obtained for a given image signal rate. Table 1 is to be understood as an example of a set of acquisition modes wherebetween switching over can take place. The Table does not include acquisition parameters such as the X-ray pulse intensity, the anode voltage of the X-ray tube, etc.

It is notably when the image acquisition time $T_B$ is changed that image artifacts occur due to the fact that in the new mode the ratio of the charge carriers excited by the bias light in capture states to the charge carriers emitted thereby has not yet been stabilized. The image acquisition time $T_B$ then increases, the distance between the bias light pulses is also increased and on average fewer charge carriers in capture states are excited. Because the emission of captured charge carriers satisfies, like all decay processes, an exponential law (intensity=$A.\exp(-t/\tau)$, where A is a proportionality factor and t is the time elapsed since the beginning of the process), and because the time constant $\tau$ then occurring is large relative to the image acquisition time $T_B$, at the beginning of the new mode even more charge carriers are emitted than in the stabilized state. An offset-corrected dark image then exhibits an additional artifact signal after the change of mode, which artifact signal asymptotically approaches zero in the ideal case. The changing and control of at least one second exposure parameter of the detector exposure unit (for example, the exposure time $T_L$) in accordance with the invention, so that the integral light intensity applied to the detector by means of the exposure unit does not change, reduces the artifact signal.

FIG. 5 shows the behavior of examples of artifact signals without adaptation of a second exposure parameter in accordance with the invention. The value of the offset-corrected dark image signal which has been averaged across the detector is indicated therein in digital detector value units (LSB) relative to the image number (FN). It is shown for 20 images in two sequences that the change of mode took place from the image 9 to the image 10. The curve K1 shows the value for a change of the image acquisition time $T_B$ from 135 ms to 565 ms and the curve K2 belongs to a change of mode in which the pixel size was changed, that is, a combination of pixels so as to form image points. In the case of a combination of 2×2 pixels the image acquisition time $T_B$ is then reduced to approximately one half, because the column pixels can be simultaneously read out. The bias light pulse duration $T_L$, being a second exposure parameter, was not changed by the change of mode.

FIG. 6 shows curves K3 and K4 which have been measured in the same circumstances as the curves K1 and K2; the curves K1 and K3 belong to the same change of mode like K2 and K4. The bias light pulse time $T_L$ was changed in proportion to the change of the image acquisition time $T_B$ in accordance with the invention; thus, upon the change from 2×2 combined pixels to non-combined pixels a doubling of the bias light pulse duration $T_L$ was selected. It appears that in the case of the change of the image acquisition time $T_B$ a reduction of the artifact signals to very small residual artifacts could be achieved and that in the case of the change of the pixel size a less pronounced reduction of the artifact signal was obtained. This is due to the fact that other effects additionally contribute to the artifact signal in the case of a change of the pixel size.

A proportional prolongation of the bias light pulse duration $T_L$ with the same integral light quantity as in the preceding mode typically leads to a steady state which is not exactly the same, because other capture state density functions are also obtained due to the changed time intervals between the pulses, since a larger share of capture states has been vacated in the longer time interval. Consequently, the next bias light pulse encounters a different constellation of free capture states. Therefore, the dynamic steady state is not exactly the same for the same integral bias light exposure. In order to improve the changing, a change can be performed which is not directly proportional to the change of the image acquisition time $T_B$ or the change can be controlled in such a manner that the new steady state is reached in an optimum fashion. When a longer or shorter bias light pulse duration $T_L$ is adjusted for a brief period of time, which duration slowly converges towards the final value, or when the bias light pulse duration $T_L$ is adjusted so as to fluctuate at increasingly smaller distances from and around the final value, the offset-corrected signal variation can be controlled more accurately to the zero line. Change values thus controlled result in even better artifact suppression. The exact values of a change controlled in this manner can be determined in the course of the detector calibration. The detector calibration is a necessary step to determine the parameters of the detectors from defined measurements with and without X-ray exposure, which parameters are required at a later stage for the further processing of the image signals, that is, the offset value for each pixel, the gain value for each pixel, etc.

Overall, an improved X-ray apparatus is obtained which includes an X-ray detector with a detector exposure unit, the detector exposure unit being controlled by a control unit in such a manner that upon a change of acquisition mode there is achieved a reduction of image artifacts in comparison with the present state of the art. The image quality increases and enables a change of mode without risking the formation of X-ray images which are no longer suitable for medical evaluation.

The invention claimed is:

1. An X-ray apparatus for forming X-ray images, which apparatus includes
   an X-ray detector (4) for the conversion of X-rays into electrical signals,
   a detector exposure unit (5) for the emission of electromagnetic radiation in dependence on first and second exposure parameters, the value of the first exposure parameters being defined by the acquisition mode whereas the second exposure parameters are not defined by the acquisition mode, and a control unit for changing and controlling at least one second exposure parameter of the detector exposure unit (5) upon a change of the acquisition mode.

2. An X-ray apparatus as claimed in claim 1, characterized in that the X-ray apparatus additionally includes an X-ray source (1).

3. An X-ray apparatus as claimed in claim 1 or 2, characterized in that the control unit (13) is additionally arranged to control at least one further component (1, 4) of the X-ray apparatus.

4. An X-ray apparatus as claimed in claim 1, characterized in that the image acquisition time and/or the X-ray exposure time and/or the detector resolution are acquisition parameters, which determine the acquisition mode.

5. An X-ray detector as claimed in claim 1, characterized in that the control unit (13) is arranged to change and control the exposure intensity and/or exposure time and/or exposure wavelength composition of the detector exposure unit (5).

6. An X-ray apparatus as claimed in claim 1, characterized in that an exposure parameter is changed and controlled in proportion to the change of an acquisition parameter.

7. An X-ray apparatus as claimed in claim 1, characterized in that the change and control of an exposure parameter satisfies a function, which converges towards a constant final value as from the change of the acquisition mode.

8. An X-ray apparatus as claimed in claim 1, characterized in that the control unit (13) is arranged to read out values for changing and controlling the exposure parameters from a storage medium (15).

9. An X-ray apparatus as claimed in claim 1, characterized in that the detector exposure unit (5) is active only within the electronic reset phase of the X-ray detector (4).

10. A method of converting X-rays into electrical signals by means of an X-ray apparatus for forming X-ray images, which method includes the steps of:

irradiating an X-ray detector (4) by means of X-rays, additionally irradiating the X-ray detector, in dependence on first and second exposure parameters, by means of a detector exposure unit (5), which emits electromagnetic radiation, the value of the second exposure parameters are not defined by the acquisition mode, changing and controlling at least one of the second exposure parameters of the detector exposure unit (5) after a change of the acquisition mode, reading out the electrical signals produced by the X-ray detector (4).

* * * * *